US012754174B2

(12) United States Patent
Hampton

(10) Patent No.: US 12,754,174 B2
(45) Date of Patent: Oct. 6, 2026

(54) METHODS OF DETECTING PERFLUOROALKYL OR POLYFLUOROALKYL SUBSTANCES

(71) Applicant: Shaw Industries Group, Inc., Dalton, GA (US)

(72) Inventor: Clay Hampton, Dalton, GA (US)

(73) Assignee: Shaw Industries Group, Inc., Dalton, GA (US)

( * ) Notice: Subject to any disclaimer, the term of this patent is extended or adjusted under 35 U.S.C. 154(b) by 0 days.

(21) Appl. No.: 19/390,329

(22) Filed: Nov. 14, 2025

(65) Prior Publication Data

US 2026/0185971 A1 Jul. 2, 2026

Related U.S. Application Data

(63) Continuation of application No. PCT/US2025/040369, filed on Aug. 1, 2025.

(60) Provisional application No. 63/775,605, filed on Mar. 21, 2025, provisional application No. 63/739,245, filed on Dec. 27, 2024.

(51) Int. Cl.
*G01N 31/00* (2006.01)
*G01N 33/00* (2006.01)

(52) U.S. Cl.
CPC ....... *G01N 31/005* (2013.01); *G01N 33/0049* (2013.01); *Y10T 436/196666* (2015.01)

(58) Field of Classification Search
CPC ............... G01N 31/005; G01N 31/224; G01N 33/0049; G01N 33/0052; G01N 33/182; G01N 30/02; G01N 30/06; G01N 30/26; G01N 30/62; Y10T 436/19; Y10T 436/193333; Y10T 436/196666; Y10T 436/24; Y10T 436/25; Y10T 436/25375; Y10T 436/255
USPC ......... 436/85, 124, 125, 126, 161, 173, 174, 436/177, 178
See application file for complete search history.

(56) References Cited

U.S. PATENT DOCUMENTS

| | | | | |
|---|---|---|---|---|
| 11,993,683 | B1 | 5/2024 | Dedick et al. | |
| 2018/0036552 | A1 | 2/2018 | Vecchio et al. | |
| 2019/0241452 | A1 | 8/2019 | Ball | |
| 2020/0155885 | A1* | 5/2020 | Strathmann | A62D 3/36 |
| 2022/0371920 | A1* | 11/2022 | Xiong | C02F 1/70 |
| 2023/0049247 | A1 | 2/2023 | Dejarme et al. | |
| 2025/0019265 | A1* | 1/2025 | Liu | C02F 1/32 |

FOREIGN PATENT DOCUMENTS

WO WO 2025/217656 A2 10/2025

OTHER PUBLICATIONS

Schlesinger et al. Abstract from Abstracts of Papers, ACS Spring Meeting 2023, Indianapolis, IN, United States, Mar. 26-30, 2023.*
International Search Report and Written Opinion in International Appln. No. PCT/US2025/040369, mailed on Oct. 15, 2025, 11 pages.

* cited by examiner

*Primary Examiner* — Maureen Wallenhorst
(74) *Attorney, Agent, or Firm* — Fish & Richardson P.C.

(57) ABSTRACT

Methods of detecting the presence of one or more fluorinated compounds, including perfluoroalkyl or polyfluoroalkyl substance (PFAS), in a sample are provided. The methods include the steps of chemically treating a sample with an oxidizing agent, such as a persulfate solution or Fenton's reagent, collecting the fluorinated compounds, and detecting the fluorinated compounds using analytical methods.

28 Claims, No Drawings

METHODS OF DETECTING PERFLUOROALKYL OR POLYFLUOROALKYL SUBSTANCES

CLAIM OF PRIORITY

This application is a continuation application of PCT/US2025/040369, filed Aug. 1, 2025, which claims the benefit of U.S. Provisional Patent Application Ser. No. 63/739,245, filed on Dec. 27, 2024, and U.S. Provisional Patent Application Ser. No. 63/775,605, filed on Mar. 21, 2025. The entire contents of each the foregoing are incorporated by reference herein in their entireties.

TECHNICAL FIELD

This document relates to methods of detecting the presence of one or more perfluoroalkyl or polyfluoroalkyl substance (PFAS) in a sample comprising chemically treating a sample and detecting the fluorinated compounds using analytical methods.

BACKGROUND

Perfluoroalkyl or polyfluoroalkyl substance (PFAS) compounds are a class of organofluorine chemical compounds, which comprise multiple fluorine atoms attached to carbon chains. PFAS compounds are a common industrial and commercial pollutant, and pose environmental and human health threats.

The identity and concentration of some PFAS compounds can be detected through existing analytical techniques, but many cannot be detected or measured. For example, there are estimated to be millions of different PFAS compounds produced each year, but existing the U.S. Environmental Protection Agency (EPA) detection methods, such as EPA method 537.1 or EPA method 1633A, are only able to detect a relatively small number of different PFAS compounds.

One method to improve detection of PFAS compounds is to first chemically treat a sample which may contain PFAS compounds to convert these compounds to PFAS compounds with known analytical standards. For example, the total oxidizable precursor assays (TOP or TOPA) chemically oxidize PFAS compounds to form perfluoroalkyl or polyfluoroalkyl acid analogs, which are easier to detect using existing analytical techniques. However, such methods may not oxidize all PFAS compounds present, or may result in partial or incomplete oxidation of PFAS compounds, leading to under-detection of PFAS compounds present in a sample.

Therefore, there is a need for new methods to detect the identity and concentration of PFAS compounds in samples with high selectivity and sensitivity.

SUMMARY

Provided in the present disclosure are methods of detecting the presence of one or more perfluoroalkyl or polyfluoroalkyl substance (PFAS) compounds in a sample, comprising:

a) treating the sample with an oxidizing agent to form a mixture;

b) maintaining the mixture for a reaction time at a reaction temperature;

c) collecting fluorinated compounds formed by oxidation of the one or more PFAS compounds in step a), and optionally b), in an aqueous mixture;

and d) detecting the fluorinated compounds by a process comprising subjecting the mixture obtained in step c) to EPA method 537.1 or EPA method 1633;

wherein at least some of the fluorinated compounds detected in step d) are different from fluorinated compounds detected by a second method that does not comprise steps a) to c).

In some embodiments, the sample further comprises one or more surfactants.

In some embodiments, the oxidizing agent in step a) is a source of OH radicals.

In some embodiments, the oxidizing agent in step a) is a persulfate or a Fenton's reagent.

In some embodiments, the oxidizing agent in step a) is a persulfate.

In some embodiments, the persulfate is sodium persulfate, potassium persulfate, ammonium persulfate, sodium peroxomonosulfate, or potassium peroxymonosulfate.

In some embodiments, the persulfate is sodium persulfate.

In some embodiments, when the oxidizing agent is a persulfate, the sample is treated with a base to form a pre-mixture, and the pre-mixture is treated with an oxidizing agent to form a mixture.

In some embodiments, the base is an aqueous base.

In some embodiments, the base is a hydroxide.

In some embodiments, the base is potassium hydroxide (KOH), sodium hydroxide (NaOH), barium hydroxide (Ba(OH)2), cesium hydroxide (Cs(OH)2), strontium hydroxide (Sr(OH)2), calcium hydroxide (Ca(OH)2), lithium hydroxide (LiOH), or rubidium hydroxide (RbOH).

In some embodiments, the base is potassium hydroxide (KOH) or sodium hydroxide (NaOH).

In some embodiments, the base is present in a concentration of about 0.1 M to about 10 M.

In some embodiments, the base is aqueous sodium hydroxide (NaOH) at a concentration of about 0.1 M to about 10 M.

In some embodiments, the base is aqueous sodium hydroxide (NaOH) at a concentration of about 1 M.

In some embodiments, step b) further comprises heating the mixture.

In some embodiments, the reaction temperature in step b) is from about 50° C. to about 100° C.

In some embodiments, the reaction temperature in step b) is about 75° C.

In some embodiments, the reaction time in step b) is from about 6 h to about 48 h.

In some embodiments, the reaction time in step b) is about 24 h.

In some embodiments, the oxidizing agent in step a) is a Fenton's reagent.

In some embodiments, step b) further comprises cooling the mixture to a first reaction temperature and then heating the mixture to a second reaction temperature.

In some embodiments, the first reaction temperature in step b) is from about 0° C. to about 15° C.

In some embodiments, the first reaction temperature in step b) is about 5° C.

In some embodiments, the second reaction temperature in step b) is from about 15° C. to about 25° C.

In some embodiments, the second reaction temperature in step b) is about 20° C.

In some embodiments, the reaction time in step b) is from about 10 min to about 4 h.

In some embodiments, the reaction time in step b) is about 2 h.

In some embodiments, the base is aqueous sodium hydroxide (NaOH) at a concentration of about 0.1 M to about 10 M; the oxidizing agent in step a) is sodium persulfate; the reaction temperature in step b) is from about 50° C. to 100° C.; and the reaction time in step b) is from about 6 h to about 48 h.

In some embodiments, the base is aqueous sodium hydroxide (NaOH) at a concentration of about 1 M; the oxidizing agent in step a) is a sodium persulfate; the reaction temperature in step b) is about 75° C.; and the reaction time in step b) is about 24 h.

In some embodiments, the oxidizing agent in step a) is a Fenton's reagent; step b) further comprises cooling the mixture to a first reaction temperature of from about 0° C. to about 15° C. and then heating the mixture to a second reaction temperature of from about 15° C. to about 25° C.; and the reaction time in step b) is from about 10 min to 4 h.

In some embodiments, the oxidizing agent in step a) is a Fenton's reagent; step b) further comprises cooling the mixture to a first reaction temperature of about 5° C. and then heating the mixture to a second reaction temperature of about 20° C.; and the reaction time in step b) is about 2 h.

In some embodiments, the aqueous mixture in step c) is an aqueous solution, a suspension, or on solid polymer chips.

In some embodiments, the aqueous mixture in step c) is an aqueous solution.

In some embodiments, the method comprises subjecting a sample to EPA method 537.1 or EPA method 1633.

DETAILED DESCRIPTION

The present disclosure relates to methods of detecting the presence of one or more PFAS compounds in a sample, comprising: a) treating the sample with an oxidizing agent to form a mixture; b) maintaining the mixture for a reaction time at a reaction temperature; c) collecting fluorinated compounds formed by oxidation of the one or more PFAS compounds in step a), and optionally b), in an aqueous mixture; and d) detecting the fluorinated compounds by a process comprising subjecting the mixture obtained in step c) to EPA method 537.1 or EPA method 1633; wherein at least some of the fluorinated compounds detected in step d) are different from fluorinated compounds detected by a second method that does not comprise steps a) to c).

The treatment of a sample which may contain PFAS compounds with an oxidizing agent may provide advantages over methods of detecting the presence of PFAS compounds that do not include any treatment step or steps. First, the disclosed methods may convert many PFAS compounds that are otherwise undetectable using conventional methods into detectable PFAS compounds. Second, the use of strong oxidizing agents, such as a persulfate or a Fenton's reagent, may result in the oxidation of PFAS compounds that are not oxidizable or detectable using conventional methods.

In some embodiments, the sample is a composition, a solution, or a solid sample.

In some embodiments, the sample is a composition.

In some embodiments, the sample is a solution.

In some embodiments, the sample is a solid sample.

In some embodiments, the sample further comprises one or more surfactants.

In some embodiments, the one or more surfactants are an anionic surfactant, a cationic surfactant, a nonionic surfactant, an amphoteric surfactant, or a combination thereof.

In some embodiments, at least one surfactant is an anionic surfactant.

In some embodiments, the anionic surfactant is a sulfonate surfactant.

In some embodiments, at least one anionic surfactant is an alkyl sulfate, a docusate (dioctyl sodium sulfosuccinate), a perfluorooctanesulfonate (PFOS), a perfluorobutanesulfonate, an alkyl-aryl ether phosphates, an alkyl ether phosphates, a carboxylate, or an alkylbenzene sulfonate.

In some embodiments, at least one anionic surfactant is an alkylbenzene sulfonate.

In some embodiments, the anionic surfactant is ammonium lauryl sulfate, sodium lauryl sulfate (sodium dodecyl sulfate, SLS, or SDS), sodium laureth sulfate (sodium lauryl ether sulfate or SLES), sodium myreth sulfate, sodium stearate, lauroyl sarcosinate, perfluorononanoate, sodium dodecylbenzenesulfonate, or perfluorooctanoate (PFOA or PFO).

In some embodiments, at least one surfactant is a cationic surfactant.

In some embodiments, at least one cationic surfactant is a pH-dependent primary amine, a pH-dependent secondary amine, a pH-dependent tertiary amine, or a permanently charged quaternary ammonium salt.

In some embodiments, at least one cationic surfactant is octenidine dihydrochloride, cetrimonium bromide (CTAB), cetylpyridinium chloride (CPC), benzalkonium chloride (BAC), benzethonium chloride (BZT), dimethyldioctadecylammonium chloride, or dioctadecyldimethylammonium bromide (DODAB).

In some embodiments, at least one surfactant is a nonionic surfactant.

In some embodiments, at least one nonionic surfactant is an ethoxylate, a fatty alcohol ethoxylate, a narrow-range ethoxylate, an ctaethylene glycol monododecyl ether, a pentaethylene glycol monododecyl ether, an alkylphenol ethoxylate (APE or APEO), a nonoxynol, a fatty acid ethoxylate, an ethoxylated amine, a fatty acid amide, a terminally blocked ethoxylate, a poloxamer, a fatty acid esters of polyhydroxy compound, a fatty acid ester of glycerol, a fatty acid ester of sorbitol, a sorbitan ester (a Span), a Tween, a fatty acid ester of sucrose, an alkyl polyglucoside, or an alkyl polyglycoside.

In some embodiments, at least one nonionic surfactant is Triton X-100, glycerol monostearate, glycerol monolaurate, polyethoxylated tallow amine, cocamide monoethanolamine, cocamide diethanolamine, Tween 20, Tween 40, Tween 60, Tween 80, sorbitan monolaurate, sorbitan monostearate, sorbitan tristearate, decyl glucoside, lauryl glucoside, or octyl glucoside.

In some embodiments, at least one surfactant is an amphoteric surfactant.

In some embodiments, at least one amphoteric surfactant is a sulfonate, a betaine, or a sphingomyelin.

In some embodiments, at least one amphoteric surfactant is (3-[(3-cholamidopropyl)dimethylammonio]-1-propanesulfonate), cocamidopropyl hydroxysultaine, cocamidopropyl betaine, phosphatidylserine, phosphatidylethanolamine, phosphatidylcholine, lauryldimethylamine oxide, or myristamine oxide.

In some embodiments wherein a sample comprises a surfactant, the presence of the surfactant results in a standard EPA method, such as EPA method 537.1 or EPA method 1633, not detecting the presence of one or more PFAS in the sample. In some embodiments, one of the advantages of the methods disclosed herein lies in the improved detection of PFAS in samples that contain the surfactant. In some embodiments, the surfactant comprises 6:2 fluorotelomer sulfonamide, perfluorooctanesulfonate (PFOS), or 5:3 fluorotelomer carboxylic acid (FTCA). In some embodiments, the PFAS comprises perfluorobutanoic acid (PFBA), perfluorohexanoic acid (PFHxA), or perfluoropentanoic acid (PFPeA). In some embodiments, the sample that comprises perfluorobutanoic acid (PFBA), perfluorohexanoic acid (PFHxA), or perfluoropentanoic acid (PFPeA) and is not detected by EPA method 537.1 or by EPA method 1633 but is detected by a method disclosed herein. In some embodiments, the sample that comprises a surfactant selected from 6:2 fluorotelomer sulfonamide, perfluorooctanesulfonate (PFOS), or 5:3 fluorotelomer carboxylic acid (FTCA) is not detected by EPA method 537.1 or by EPA method 1633 but is detected by a method disclosed herein. In some embodiments, the sample that comprises perfluorobutanoic acid (PFBA), perfluorohexanoic acid (PFHxA), or perfluoropentanoic acid (PFPeA) and a surfactant selected from 6:2 fluorotelomer sulfonamide, perfluorooctanesulfonate (PFOS), or 5:3 fluorotelomer carboxylic acid (FTCA) is not detected by EPA method 537.1 or by EPA method 1633 but is detected by a method disclosed herein.

In some embodiments, the oxidizing agent in step a) is a source of OH radicals.

In some embodiments, the oxidizing agent in step a) is a persulfate or a Fenton's reagent.

In some embodiments, the oxidizing agent in step a) is a persulfate.

In some embodiments, the oxidizing agent in step a) is a Fenton's reagent.

In some embodiments, a Fenton's reagent is an aqueous solution comprising an oxidant and an iron salt.

In some embodiments, the oxidant is a peroxide. In some embodiments, the oxidant is hydrogen peroxide.

In some embodiments, the iron salt is an iron (II) salt. In some embodiments, the iron salt is iron (II) sulfate.

In some embodiments, a Fenton's reagent is an aqueous solution comprising hydrogen peroxide and iron (II) sulfate ($FeSO_4$).

In some embodiments, the persulfate is sodium persulfate, potassium persulfate, ammonium persulfate, sodium peroxomonosulfate, or potassium peroxymonosulfate.

In some embodiments, the persulfate is sodium persulfate.

In some embodiments, when the oxidizing agent is a persulfate, the sample is treated with a base to form a pre-mixture, and the pre-mixture is treated with an oxidizing agent to form a mixture.

In some embodiments, the base is an aqueous base.

In some embodiments, the base is a hydroxide.

In some embodiments, the base is potassium hydroxide (KOH), sodium hydroxide (NaOH), barium hydroxide ($Ba(OH)_2$), cesium hydroxide ($Cs(OH)_2$), strontium hydroxide ($Sr(OH)_2$), calcium hydroxide ($Ca(OH)_2$), lithium hydroxide (LiOH), or rubidium hydroxide (RbOH).

In some embodiments, the base is potassium hydroxide (KOH) or sodium hydroxide (NaOH). In some embodiments, the base is potassium hydroxide (KOH).

In some embodiments, the base is sodium hydroxide (NaOH).

In some embodiments, the base is present in a concentration of about 0.1 M to about 10 M, about 0.1 M to about 9 M, about 0.1 M to about 8 M, about 0.1 M to about 7 M, about 0.1 M to about 6 M, about 0.1 M to about 5 M, about 0.1 M to about 4 M, about 0.1 M to about 3 M, about 0.1 M to about 2 M, about 0.1 M to about 1 M, or about 0.1 M to about 5 M.

In some embodiments, the base is present in a concentration of about 0.1 M to about 10 M, about 0.5 M to about 10 M, about 1 M to about 10 M, about 2 M to about 10 M, about 3 M to about 10 M, about 4 M to about 10 M, about 5 M to about 10 M, about 6 M to about 10 M, about 7 M to about 10 M, about 8 M to about 10 M, or about 9 M to about 10 M.

In some embodiments, the base is present in a concentration of about 0.1 M to about 5 M, about 0.5 M to about 2 M, about 0.75 M to about 1.5 M, or about 0.9 M to about 1.1 M.

In some embodiments, the base is present in a concentration of about 0.1 M, about 0.5 M, about 0.75 M, about 0.9 M, about 1 M, about 2 M, about 3 M, about 4 M, about 5 M, about 6 M, about 7 M, about 8 M, about 9 M, or about 10 M.

In some embodiments, the base is present in a concentration of about 1 M.

In some embodiments, the base is aqueous sodium hydroxide (NaOH) at a concentration of about 0.1 M to about 10 M.

In some embodiments, the base is aqueous sodium hydroxide (NaOH) at or above a concentration of about 1 M.

In some embodiments, the base is aqueous sodium hydroxide (NaOH) at a concentration of about 1 M. In some embodiments, step a) is performed at room temperature.

In some embodiments, step a) is performed at about 0° C. to about 15° C. In some embodiments, step a) is performed at about 0° C. to about 10° C. In some embodiments, step a) is performed at about 0° C. In some embodiments, step a) is performed at about 5° C. In some embodiments, step a) is performed at about 10° C. In some embodiments, step a) is performed at about 15° C. In some embodiments, step a) is performed at about 20° C. In some embodiments, step a) is performed at about 25° C.

In some embodiments, when the oxidizing agent is a persulfate, step b) further comprises heating the mixture.

In some embodiments, the reaction temperature in step b) is from about 50° C. to about 100° C., about 50° C. to about 90° C., about 50° C. to about 80° C., about 50° C. to about 70° C., or about 50° C. to about 60° C.

In some embodiments, the reaction temperature in step b) is from about 50° C. to about 100° C., about 60° C. to about 70° C., about 50° C. to about 80° C., or about 0° C. to about 100° C.

In some embodiments, the reaction temperature in step b) is from about 50° C. to about 100° C., about 60° C. to about 90° C., or about 70° C. to about 80° C.

In some embodiments, the reaction temperature in step b) is from about 50° C. to about 100° C.

In some embodiments, the reaction temperature in step b is about 50° C., about 55° C., about 60° C., about 65° C., about 70° C., about 75° C., about 80° C., about 85° C., about 90° C., about 95° C., or about 100° C.

In some embodiments, the reaction temperature in step b) is about 75° C.

In some embodiments, the reaction time in step b) is from about 6 h to about 48 h.

In some embodiments, the reaction time in step b) is from about 6 h to about 48 h, about 8 h to about 40 h, about 12 h to about 36 h, about 16 h to about 32 h, about 20 h to about 28 h, or about 22 h to about 26 h.

In some embodiments, the reaction time in step b) is from about 6 h to about 48 h, about 6 h to about 40 h, about 6 h to about 36 h, about 6 h to about 32 h, about 6 h to 28 h, about 6 h to about 24 h, about 6 h to about 20 h, about 6 h to about 16 h, about 6 h to about 12 h, or about 6 h to about 8 h.

In some embodiments, the reaction time in step b) is from about 6 h to about 48 h, about 8 h to about 48 h, about 12 h to about 48 h, about 16 h to about 48 h, about 20 h to about 48 h, about 24 h to about 48 h, about 28 h to about 48 h, about 32 h to about 48 h, about 36 h to about 48 h, about 40 h to about 48 h, or about 44 h to about 48 h.

In some embodiments, the reaction time in step b) is about 6 h, about 8 h, about 12 h, about 16 h, about 20 h, about 24 h, about 28 h, about 32 h, about 36 h, about 40 h, about 42 h, about 44 h, or about 48 h.

In some embodiments, the reaction time in step b) is about 24 h.

In some embodiments, the oxidizing agent in step a) is a Fenton's reagent.

In some embodiments, step b) further comprises cooling the mixture to a first reaction temperature and then heating the mixture to a second reaction temperature.

In some embodiments, the first reaction temperature in step b) is from about 0° C. to about 15° C.

In some embodiments, the first reaction temperature in step b) is about 0° C., about 5° C., about 10° C., or about 15° C.

In some embodiments, the first reaction temperature in step b) is about 5° C.

In some embodiments, the second reaction temperature in step b) is from about 15° C. to 25° C.

In some embodiments, the second reaction temperature in step b) is about 15° C., about 20° C., or about 25° C.

In some embodiments, the second reaction temperature in step b) is about 20° C.

In some embodiments, the reaction time in step b) is from about 10 min to about 4 h.

In some embodiments, the reaction time in step b) is about 2 h.

In some embodiments, the base is aqueous sodium hydroxide (NaOH) at a concentration of about 0.1 M to about 10 M; the oxidizing agent in step a) is a sodium persulfate; the reaction temperature in step b) is from about 50° C. to about 100° C.; and the reaction time in step c) is from about 6 h to about 48 h.

In some embodiments, the base is aqueous sodium hydroxide (NaOH) at a concentration of about 1 M; the oxidizing agent in step a) is a sodium persulfate; the reaction temperature in step c) is about 75° C.; and the reaction time in step b) is about 24 h.

In some embodiments, the oxidizing agent in step a) is a Fenton's reagent; and step b) further comprises cooling the mixture to a first reaction temperature of from about 0° C. to about 15° C. and then heating the mixture to a second reaction temperature of from about 15° C. to about 25° C.

In some embodiments, the oxidizing agent in step a) is a Fenton's reagent; and step c) further comprises cooling the mixture to a first reaction temperature of about 5° C. and then heating the mixture to a second reaction temperature of about 20° C.

In some embodiments, the aqueous mixture in step b) is an aqueous solution, a suspension, or on solid polymer chips.

In some embodiments, the aqueous mixture in step b) is an aqueous solution.

In some embodiments, the aqueous mixture in step b) is a suspension.

In some embodiments, the aqueous mixture in step b) is on solid polymer chips.

In some embodiments, the second method comprises subjecting a sample to EPA method 537.1 or EPA method 1633.

EPA method 537.1 is an analytical method that may be used to determine the presence of certain PFAS compounds in drinking water by solid phase extraction and liquid chromatography/tandem mass spectrometry. EPA method 537.1 is described below in further detail.

EPA method 1633 is an analytical method that may be used to determine the presence of certain PFAS compounds in aqueous, solid, biosolid, and tissue samples by liquid chromatography/tandem mass spectrometry. EPA method 1633 is described below in further detail.

In some embodiments, the second method comprises subjecting a sample to EPA method 537.1.

EPA method 537.1 is described in detail in EPA Document #: EPA/600/R-20/006, which is incorporated herein by reference in its entirety.

In some embodiments, the second method comprises subjecting a sample comprising the surfactant to EPA method 1633.

EPA method 1633 is described in detail in EPA Document #: EPA 821-D-21-001, which is incorporated herein by reference in its entirety.

In some embodiments, the PFAS compounds in the sample comprise one PFAS compound present in a concentration of about 50 parts per trillion (ppt) or greater.

In some embodiments, the PFAS compounds in the sample comprise one PFAS compound present in a concentration of about 50 ppt to about 100,000 ppt.

In some embodiments, the PFAS compounds in the sample comprise one or more PFAS compounds each present in a concentration of about 50 ppt or greater.

In some embodiments, the PFAS compounds in the sample comprise one or more PFAS compounds each present in a concentration of about 50 ppt to about 100,000 ppt.

In some embodiments, the sample comprises about a 1:2 ratio of surfactant to PFAS compounds or less.

In some embodiments, at least one of the fluorinated compounds formed by oxidation of the one or more PFAS compounds in step a), are derivatives of the one or more PFA compounds in the sample, fragments of the one or more PFA compounds in the sample, or a combination thereof.

In some embodiments, at least one of the derivatives of the one or more PFA compounds in the sample comprise at least one additional sulfonic acid, sulfate, carboxylic acid, or carboxylate functional group compared to the PFAS compounds in the sample.

In some embodiments, at least one of the derivatives of the one or more PFA compounds in the sample comprise at least one additional sulfonic acid functional group compared to the PFAS compounds in the sample.

In some embodiments, at least one of the derivatives of the one or more PFA compounds in the sample comprise at least one additional sulfate functional group compared to the PFAS compounds in the sample.

In some embodiments, at least one of the derivatives of the one or more PFA compounds in the sample comprise at least one additional carboxylic acid functional group compared to the PFAS compounds in the sample.

In some embodiments, at least one of the derivatives of the one or more PFA compounds in the sample comprise at least one additional carboxylate functional group compared to the PFAS compounds in the sample.

In some embodiments, at least one of the fragments of the one or more PFA compounds in the sample are formed from the degradation of the one or more PFA compounds in the sample to two or more different compounds.

In some embodiments, at least one of the fragments of the one or more PFA compounds in the sample are formed from the degradation of the one or more PFA compounds in the sample to two or more different compounds each having fewer carbon atoms than the degraded PFAS compound.

Non-limiting examples of PFAS compounds, the fluorinated compounds formed by oxidation of the one or more PFAS compounds, and/or the fluorinated compounds detected are hexafluoropropylene oxide dimer acid (HFPO-DA), N-ethyl perfluorooctanesulfonamidoacetic acid (NEtFOSAA), N-methyl perfluorooctanesulfonamidoacetic acid (NMeFOSAA), perfluorobutanesulfonic acid (PFBS), perfluorodecanoic acid (PFDA), perfluorododecanoic acid (PFDoA), perfluoroheptanoic acid (PFHpA), perfluorohexanesulfonic acid (PFHxS), perfluorohexanoic acid (PFHxA), perfluorononanoic acid (PFNA), perfluorooctanesulfonic acid (PFOS), perfluorooctanoic acid (PFOA), perfluorotetradecanoic acid (PFTA), perfluorotridecanoic acid (PFTrDA), perfluoroundecanoic acid (PFUnA), 11-chloroeicosafluoro-3-oxaundecane-1-sulfonic acid (11Cl-PF3OUdS), 9-chlorohexadecafluoro-3-oxanonane-1-sulfonic acid (9Cl-PF3ONS), 4,8-dioxa-3H-perfluorononanoic acid (ADONA), perfluorobutanoic acid (PFBA), perfluoropentanoic acid (PFPeA), perfluoroheptanoic acid (PFHpA), perfluorotetradecanoic acid (PFTeDA), perfluoropentanesulfonic acid (PFPeS), perfluoroheptanesulfonic acid (PFHpS), perfluorononanesulfonic acid (PFNS), perfluorodecanesulfonic acid (PFDS), perfluorododecanesulfonic acid (PFDoS), 1H,1H, 2H, 2H-Perfluorohexane sulfonic acid (4:2FTS), 1H,1H, 2H, 2H-Perfluorooctane sulfonic acid (6:2FTS), 1H,1H, 2H, 2H-Perfluorodecane sulfonic acid (8:2FTS), perfluorooctanesulfonamide (PFOSA), N-methyl perfluorooctanesulfonamide (NMeFOSA), N-ethyl perfluorooctanesulfonamide (NEtFOSA), N-methyl perfluorooctanesulfonamidoethanol (NMeFOSE), N-ethyl perfluorooctanesulfonamidoethanol (NEtFOSE), perfluoro-3-methoxypropanoic acid (PFMPA), perfluoro-4-methoxybutanoic acid (PFMBA), nonafluoro-3,6-dioxaheptanoic acid (NFDHA), perfluoro(2-ethoxyethane) sulfonic acid (PFEESA), 3-perfluoropropyl propanoic acid (3:3FTCA), 2H,2H,3H,3H-Perfluorooctanoic acid (5:3FTCA), and 3-perfluoroheptyl propanoic acid (7:3FTCA).

Non-limiting examples of PFAS compounds, the fluorinated compounds formed by oxidation of the one or more PFAS compounds, and/or the fluorinated compounds detected in are shown in Table A.

TABLE A

Exemplary PFAS Compounds and their CAS Numbers

| Compound Name and/or Description | CAS Registry No. |
|---|---|
| 1H,1H,2'H-Perfluorodipropyl ether | 1000-28-8 |
| 1H,2H-Hexafluorocyclopentene | 1005-73-8 |
| 1H,1H,2H,2H-Perfluorodecyltriethoxysilane | 101947-16-4 |
| 1H,1H,2H,2H-Perfluorododecyltrichlorosilane | 102488-49-3 |
| 3-(Perfluoroisopropyl)-(2E)-difluoropropenoic acid | 103229-89-6 |
| 1H,1H,8H-Perfluoro-1-octanol | 10331-08-5 |
| 2,2,3,3-Tetrafluoropropyl trifluoroacetate | 107551-72-4 |
| 5H,5H-Perfluoro-4,6-nonanedione | 113116-18-0 |
| NVHOS | 1132933-86-8 |
| Perfluoro-2-ethoxyethanesulfonic acid (PFEESA) | 113507-82-7 |
| (1S,4S)-3-(Heptafluorobutyryl)camphor | 115224-00-5 |
| 10:2 FTS | 120226-60-0 |
| 3-(Perfluoro-2-butyl)propane-1,2-diol | 125070-38-4 |
| Methyl 3-chloroperfluoropropanoate | 127589-63-3 |
| 1H,1H,8H,8H-Perfluoro-3,6-dioxaoctane-1,8-diol | 129301-42-4 |
| Methyl perfluoropentanoate | 13038-26-1 |
| PMPA | 13140-29-9 |
| Methyl perfluoro(2-propoxypropanoate) | 13140-34-6 |
| Hexafluoroisopropyl methyl ether | 13171-18-1 |

TABLE A-continued

Exemplary PFAS Compounds and their CAS Numbers

| Compound Name and/or Description | CAS Registry No. |
|---|---|
| 3-Methoxyperfluoro(2-methylpentane) | 132182-92-4 |
| Methyl 2H,2H,3H,3H-perfluoroheptanoate | 132424-36-3 |
| Perfluoro-2-methyl-3-oxahexanoic acid (HFPO-DA) | 13252-13-6 |
| Perfluoro-2,5-dimethyl-3,6-dioxanonanoic acid | 13252-14-7 |
| PFECHS | 133201-07-7 |
| 1-(Perfluorohexyl)octane | 133331-77-8 |
| Perfluorooctane sulfonamido amine | 13417-01-1 |
| Nonafluoropentanamide | 13485-61-5 |
| (Perfluoropropyl)methyl methacrylate | 13695-31-3 |
| Perfluoro-3,6-dioxadecanoic acid | 137780-69-9 |
| 2H,3H-Perfluoropentane | 138495-42-8 |
| 8H-Perfluorooctanoic acid | 13973-14-3 |
| 4-(Perfluorobutyl)-2-butanone | 140834-64-6 |
| 4-(1H,1H,2H,2H-Perfluorodecylthio)phenol | 142623-70-9 |
| 1H,1H-Perfluoro-2,5-dimethyl-3,6-dioxanonan-1-ol | 14548-74-4 |
| 1H,1H-Perfluoro-3,6,9-trioxadecan-1-ol | 147492-57-7 |
| 3-(Perfluoroethyl)propanol | 148043-73-6 |
| Trifluoromethanesulfonic acid | 1493-13-6 |
| (Perfluorooctyl)propyl acetate | 150225-00-6 |
| 3:2 Fluorotelomer iodide | 1513-88-8 |
| Hexafluoro-2-methyl-2-propanol | 1515-14-6 |
| Perfluoro-3,6-dioxaheptanoic acid (NFDHA) | 151772-58-6 |
| Perfluoro-3,6,9-trioxadecanoic acid | 151772-59-7 |
| Allyl perfluoroisopropyl ether | 15242-17-8 |
| 1H,1H,2H-Perfluorocyclopentane | 15290-77-4 |
| 11-(Perfluoro-n-octyl)undec-10-en-1-ol | 15364-19-9 |
| 7H-Perfluoroheptanoic acid | 1546-95-8 |
| 3,3-Bis(trifluoromethyl)-3-hydroxypropionic acid | 1547-36-0 |
| N,N-dimethyl-2H-perfluoroethanamine | 1550-50-1 |
| 2-Iodo-1h,1h,2h,3h,3h-perfluorodecan-1-ol | 16083-64-0 |
| (Perfluoro-3-methylbutyl)-2-hydroxypropyl acrylate | 16083-76-4 |
| Perfluoro(4-methyl-3,6-dioxaoct-7-ene)sulfonyl fluoride | 16090-14-5 |
| 6-(Perfluorohexyl)hexanol | 161981-35-7 |
| 2-Amino-2H-perfluoropropane | 1619-92-7 |
| Perfluoropropyl trifluorovinyl ether | 1623-05-8 |
| Ethyl perfluorobutyl ether | 163702-05-4 |
| Perfluorobutyl methyl ether | 163702-07-6 |
| Perfluoroisobutyl methyl ether | 163702-08-7 |
| 1-Chloro-6-iodoperfluorohexane | 16486-97-8 |
| 1-Chloro-8-iodoperfluorooctane | 16486-98-9 |
| 3-(Perfluorooctyl)propanol | 1651-41-8 |
| Perfluoro-n-octadecanoic acid (PFODA) | 16517-11-6 |
| N-[(Perfluorooctylsulfonamido)propyl]-N,N,N-trimethylammonium iodide | 1652-63-7 |
| (2H-Perfluoroethyl)(1H,1H,3H-perfluoropropyl)ether | 16627-68-2 |
| 1H,1H,5H-Perfluoropentyl-1,1,2,2-tetrafluoroethylether | 16627-71-7 |
| 1-Iodo-1H,1H,2H,2H-perfluoroheptane | 1682-31-1 |
| N-Ethyl-N-(2-hydroxyethyl)perfluorooctane sulfonamide (NEtFOSE) | 1691-99-2 |
| 3H-Perfluoro-4-hydroxy-3-penten-2-one | 1694-30-0 |
| Perfluoro-3,7-dimethyloctanoic acid | 172155-07-6 |
| 2(2H-Perfluoro-2-propyl)acetic acid | 17327-33-2 |
| 2,2-Bis(trifluoromethyl)propionyl fluoride | 1735-87-1 |
| (Perfluorohexyl)ethyl acrylate | 17527-29-6 |
| (Heptafluorobutanoyl)pivaloylmethane | 17587-22-3 |
| Perfluorooctanesulfonic acid (PFOS) | 1763-23-1 |
| 3,3-Bis(trifluoromethyl)-2-propenoic acid | 1763-28-6 |
| 11-H-Perfluoroundecanoic acid | 1765-48-6 |
| 1H,1H-Heptafluorobutyl epoxide | 1765-92-0 |
| 6H-Perfluorohex-1-ene | 1767-94-8 |
| 2-(Perfluorodecyl)ethyl acrylate | 17741-60-5 |
| 1H,1H,2H,2H-Perfluorohexyl methacrylate | 1799-84-4 |
| 1,6-Divinylperfluorohexane | 1800-91-5 |
| Perfluoromethylcyclopentane | 1805-22-7 |
| 1H,1H,9H-perfluorononyl methacrylate | 1841-46-9 |
| 1,4-Dibromo-1,1,2,2-tetrafluorobutane | 18599-20-7 |
| 2-Vinyl(1-bromoperfluoroethane) | 18599-22-9 |
| (Perfluorobutyl)ethene | 19430-93-4 |
| 3-(Perfluoro-1-propyl)-1,2-propanediol | 1992-91-2 |
| ((2,2,3,3-Tetrafluoropropoxy)methyl)oxirane | 19932-26-4 |
| 2-(Perfluorooctyl)ethyl methacrylate | 1996-88-9 |
| 3-(Perfluorooctyl)propyl iodide | 200112-75-0 |
| [(Heptafluoropropyl)sulfanyl]acetic acid | 204057-69-2 |
| Fluorotelomer alcohol 4:2 | 2043-47-2 |
| 1-Iodo-1H,1H,2H,2H-perfluorononane | 2043-52-9 |

TABLE A-continued

Exemplary PFAS Compounds and their CAS Numbers

| Compound Name and/or Description | CAS Registry No. |
|---|---|
| 1-(Perfluorooctyl)-2-iodoethane | 2043-53-0 |
| 10:2 Fluorotelomer iodide | 2043-54-1 |
| 1H,1H,2H,2H-Perfluorooctyl iodide | 2043-57-4 |
| 3H,3H-Perfluoroheptane-2,4-dione | 20583-66-8 |
| Perfluoroundecanoic acid (PFUnA) | 2058-94-8 |
| Perfluoro(2-methyl-3-oxahexanoyl) fluoride | 2062-98-8 |
| 3H,3H-Perfluoro-2,4-hexanedione | 20825-07-4 |
| 3,5,6-Trichloroperfluorohexanoic acid | 2106-54-9 |
| 2-(Perfluorohexyl)ethyl methacrylate | 2144-53-8 |
| 10:2 Fluorotelomer methacrylate | 2144-54-9 |
| 4H,4H-Perfluoro-6,6-dimethylheptane-3,5-dione | 2145-68-8 |
| Hexafluoroisopropyl acrylate | 2160-89-6 |
| 1H,1H,2H-Perfluoro-1-decene | 21652-58-4 |
| 1H,1H,7H-Perfluoroheptyl methacrylate | 2261-99-6 |
| 5-Bromo-4,4,5,5-tetrafluoropentanoic acid | 234443-22-2 |
| Perfluorononanedioic acid | 23453-64-7 |
| NMeFOSAA | 2355-31-9 |
| 3-(Perfluoro-2-butyl)propanoic acid | 239463-95-7 |
| 3(Perfluoro-2-butyl)propanol | 239463-96-8 |
| Potassium perfluorooctanoate | 2395-00-8 |
| 2-Vinylperfluorobutane | 239795-57-4 |
| R-PSDA | 2416366-18-0 |
| Hydrolyzed PSDA | 2416366-19-1 |
| R-PSDCA | 2416366-21-5 |
| R-EVE | 2416366-22-6 |
| 4,4-bis(Trifluoromethyl)-4-fluoropropanoic acid | 243139-62-0 |
| 3-(Perfluoroisopropyl)-2-propenoic acid | 243139-64-2 |
| N-Methyl-N-(2-hydroxyethyl)perfluorooctanesulfonamide (NMeFOSE) | 24448-09-7 |
| 2-(Perfluorohexyl)ethylphosphonic acid | 252237-40-4 |
| 1-(Perfluoroheptyl)-2-iodopropane | 25291-12-7 |
| (Perfluoroheptyl)ethene | 25431-45-2 |
| 7:3 Fluorotelomer alcohol | 25600-66-2 |
| Hexafluoropropene oxide trimer | 2641-34-1 |
| 5H-Perfluoropentanal | 2648-47-7 |
| 2-(Perfluoropropoxy)-1H,1H-perfluoropropanol | 26537-88-2 |
| PEPA | 267239-61-2 |
| 2-(4H-Perfluorobutyl)-2-propanol | 2673-15-6 |
| Perfluoropentanoic acid (PFPeA) | 2706-90-3 |
| Perfluoropentanesulfonic acid (PFPeS) | 2706-91-4 |
| 6:2 Fluorotelomer sulfonic acid (6:2 FTS) | 27619-97-2 |
| Perfluoro-2,5,8-trimethyl-3,6,9-trioxadodecanoyl fluoride | 27639-98-1 |
| 3-(Perfluorohexyl)propanoic acid | 27854-30-4 |
| 8:2 FTCA | 27854-31-5 |
| 2-(Perfluorooctyl)ethyl acrylate | 27905-45-9 |
| Potassium perfluorooctanesulfonate | 2795-39-3 |
| Ethyl 5H-octafluoropentanoate | 2795-50-8 |
| Sodium perfluorodecanesulfonate | 2806-15-7 |
| Sevoflurane | 28523-86-6 |
| Perfluorodimethylcyclobutane | 28677-00-1 |
| (Perfluorocyclohexyl)methanol | 28788-68-3 |
| 3,5,7,8-Tetrachloroperfluorooctanoic acid | 2923-68-4 |
| PS Acid | 29311-67-9 |
| Potassium perfluorobutanesulfonate | 29420-49-3 |
| 3-Ethoxyperfluoro(2-methylhexane) | 297730-93-9 |
| 3-(Perfluoroisopropyl)propanol | 29819-73-6 |
| NEtFOSAA | 2991-50-6 |
| Perfluoro-1-butanesulfonyl chloride | 2991-84-6 |
| (6H-Perfluorohexyl)methyl acrylate | 2993-85-3 |
| Perfluoro-1,2-dimethylcyclobutane | 2994-71-0 |
| 2H-Perfluoro(2-methylpentane) | 30320-28-6 |
| Ethyl perfluorononanoate | 30377-52-7 |
| (Perfluorodecyl)ethylene | 30389-25-4 |
| Perfluoro-1,2-dimethylcyclohexane | 306-98-9 |
| Perfluorohexanoic acid (PFHxA) | 307-24-4 |
| 1H,1H-Perfluorooctylamine | 307-29-9 |
| 7:1 Fluorotelomer alcohol | 307-30-2 |
| Perfluorooctanamidine | 307-31-3 |
| Perfluorooctane | 307-34-6 |
| Perfluorooctanesulfonyl fluoride | 307-35-7 |
| 9:1 Fluorotelomer alcohol | 307-37-9 |
| Perflubrodec | 307-43-7 |
| Perfluorodecane | 307-45-9 |

TABLE A-continued

Exemplary PFAS Compounds and their CAS Numbers

| Compound Name and/or Description | CAS Registry No. |
|---|---|
| 10:1 Fluorotelomer alcohol | 307-46-0 |
| Perfluorododecanoic acid (PFDoA) | 307-55-1 |
| Perfluorododecane | 307-59-5 |
| 1H,1H,11H-Eicosafluoro-1-undecanol | 307-70-0 |
| Perfluorodecanedioic acid | 307-78-8 |
| 1H,1H-Perfluorooctyl acrylate | 307-98-2 |
| 1H,8H-Perfluorooctane | 307-99-3 |
| N,N-Diethyl-2H-perfluoropropanamine | 309-88-6 |
| Ethyl perfluorooctanoate | 3108-24-5 |
| Perfluorotributylamine | 311-89-7 |
| 2-Aminohexafluoropropan-2-ol | 31253-34-6 |
| N-Methylperfluorooctanesulfonamide (NMeFOSA) | 31506-32-8 |
| 2-(Trifluoromethoxy)ethyl trifluoromethanesulfonate | 329710-76-1 |
| Perfluoro-3,6,9-trioxatridecanoic acid | 330562-41-9 |
| 1H,1H,11H-Perfluorotetraethylene glycol | 330562-44-2 |
| 2H-Perfluoro-5-methyl-3,6-dioxanonane | 3330-14-1 |
| Perfluoro-3-(1H-perfluoroethoxy)propane | 3330-15-2 |
| 2H-Perfluoro(5,8-dimethyl-3,6,9-trioxadodecane) | 3330-16-3 |
| Flurothyl | 333-36-8 |
| Perfluoro-1,3-dimethylcyclohexane | 335-27-3 |
| Perfluoro-2-butyltetrahydrofuran | 335-36-4 |
| Perfluorohexylbromide | 335-56-8 |
| 1-Iodopentadecafluoroheptane | 335-58-0 |
| Pentadecafluorooctanoyl chloride | 335-64-8 |
| Perfluorooctanoyl fluoride | 335-66-0 |
| Perfluorooctanoic acid (PFOA) | 335-67-1 |
| 1,8-Diiodoperfluorooctane | 335-70-6 |
| Perfluorodecanoic acid (PFDA) | 335-76-2 |
| Perfluorodecanesulfonic acid (PFDS) | 335-77-3 |
| Sodium perfluorooctanoate | 335-95-5 |
| 1H,1H,7H-Dodecafluoro-1-heptanol | 335-99-9 |
| Perfluoroadipoyl chloride | 336-06-1 |
| 1H,6H-Perfluorohexane | 336-07-2 |
| Perfluorohexanedioic acid | 336-08-3 |
| Perfluorobutanoic anhydride | 336-59-4 |
| 2H-Perfluoropropanoic anhydride | 337-83-7 |
| Perfluamine | 338-83-0 |
| 2-(Perfluorooctyl)ethanthiol | 34143-74-3 |
| 2-(Perfluorobutyl)ethanethiol | 34451-25-7 |
| 2-(Perfluorohexyl)ethanethiol | 34451-26-8 |
| 8:3 Fluorotelomer carboxylic acid | 34598-33-9 |
| Perfluorooctanedioic diamide | 3492-23-7 |
| Difluoromethyl 2,2,3,3-tetrafluoropropyl ether | 35042-99-0 |
| 1,8-Divinylperfluorooctane | 35192-44-0 |
| Perfluoro-1-decene | 35328-43-9 |
| (Perfluoroethyl)methyl iodide | 354-69-8 |
| Pentafluoropropionamide | 354-76-7 |
| Perfluoro-2,3-dimethylbutane | 354-96-1 |
| Perfluoromethylcyclohexane | 355-02-2 |
| Perfluoroisohexane | 355-04-4 |
| Methyl heptafluoropropylketone | 355-17-9 |
| 2,3-Dichlorooctafluorobutane | 355-20-4 |
| 2-Perfluoropropyl-2-propanol | 355-22-6 |
| 1H,1H-Perfluoropentylamine | 355-27-1 |
| 1H,1H-Perfluoro-1-pentanol | 355-28-2 |
| 1H,1H-Perfluorohexylamine | 355-34-0 |
| 1H-Perfluorohexane | 355-37-3 |
| Perfluorohexylchloride | 355-41-9 |
| Perfluoro-1-iodohexane | 355-43-1 |
| Perfluorohexanesulfonic acid (PFHxS) | 355-46-4 |
| 1H,1H-Perfluorononylamine | 355-47-5 |
| Perfluorohept-1-ene | 355-63-5 |
| Octafluoroadipamide | 355-66-8 |
| 1H,1H,6H,6H-Perfluoro-1,6-hexanediol | 355-74-8 |
| Decafluorocyclohexene | 355-75-9 |
| 1H,1H,5H-Perfluoropentanol | 355-80-6 |
| Perfluoropentanamide | 355-81-7 |
| 1H,1H,5H-Perfluoropentyl methacrylate | 355-93-1 |
| 1-Propenylperfluoropropane | 355-95-3 |
| 3:3 Fluorotelomer carboxylic acid (3:3 FTCA) | 356-02-5 |
| 4-((Perfluorohexyl)ethyl)phenylmethanol | 356055-76-0 |
| ((Perfluorooctyl)ethyl)di(propan-2-yl)silane | 356056-15-0 |
| Methyl perfluorobutanoate | 356-24-1 |
| Ethyl perfluorobutanoate | 356-27-4 |
| Methyl 4H-perfluorobutanoate | 356-32-1 |

TABLE A-continued

Exemplary PFAS Compounds and their CAS Numbers

| Compound Name and/or Description | CAS Registry No. |
|---|---|
| Pentafluoropropanoic anhydride | 356-42-3 |
| 1H,1H-Perfluoropropyl acrylate | 356-86-5 |
| 1,2-bis(1,1,2,2-Tetrafluoroethoxy)ethane | 358-39-4 |
| Methyl 3,3,3-trifluoro-2-(trifluoromethyl)propionate | 360-54-3 |
| 1H,1H,3H-Perfluorobutyl 2-methylacrylate | 36405-47-7 |
| Perfluorobutanesulfonic anhydride | 36913-91-4 |
| (E)-Perfluoro(4-methyl-2-pentene) | 3709-71-5 |
| 1-Pentafluoroethylethanol | 374-40-3 |
| Methyl perfluoroethyl ketone | 374-41-4 |
| Perfluoro-1,3,5-trimethylcyclohexane | 374-76-5 |
| Heptafluorobutyl iodide | 374-98-1 |
| 1H,1H-Heptafluorobutylamine | 374-99-2 |
| 3:1 Fluorotelomer alcohol | 375-01-9 |
| Perfluorobutyraldehyde | 375-02-0 |
| 1-Perfluoropropylethanol | 375-14-4 |
| Heptafluorobutyryl Chloride | 375-16-6 |
| Perfluorobutyrylamidine | 375-19-9 |
| Perfluorobutanoic acid (PFBA) | 375-22-4 |
| 1-Bromoperfluorobutane | 375-48-4 |
| Perfluoro-1,4-diiodobutane | 375-50-8 |
| 2-Iodoperfluorobutane | 375-51-9 |
| Perfluorobutanesulfonyl fluoride | 375-72-4 |
| Perfluorobutanesulfonic acid (PFBS) | 375-73-5 |
| 1,6-Diiodoperfluorohexane | 375-80-4 |
| 6:1 Fluorotelomer alcohol | 375-82-6 |
| 1-Hydroperfluoroheptane | 375-83-7 |
| Perfluoroheptanoic acid (PFHpA) | 375-85-9 |
| 1-Bromopentadecafluoroheptane | 375-88-2 |
| Perfluoroheptanesulfonic Acid (PFHpS) | 375-92-8 |
| Perfluorononanoic acid (PFNA) | 375-95-1 |
| Perfluorononane | 375-96-2 |
| 1-H-Perfluorodecane | 375-97-3 |
| Perfluorotridecane | 376-03-4 |
| Perfluorotetradecanoic acid (PFTeA) | 376-06-7 |
| 1H,1H,9H-Hexadecafluoro-1-nonanol | 376-18-1 |
| Methyl perfluorooctanoate | 376-27-2 |
| 5H-Octafluoropentanoic acid | 376-72-7 |
| Perfluoropentanedioic acid | 376-73-8 |
| 1H,1H,5H-Perfluoropentyl acrylate | 376-84-1 |
| Hexafluoroamylene glycol | 376-90-9 |
| Methyl 2H,2H-perfluorobutyl ether | 376-98-7 |
| Perfluorobutanedioic acid | 377-38-8 |
| Perfluoro-3-methoxypropanoic acid (PFMPA) | 377-73-1 |
| Methyl 1H,1H-perfluoropropyl ether | 378-16-5 |
| Methyl pentafluoropropionate | 378-75-6 |
| 3H-Perfluorobutanoic acid | 379-90-8 |
| Ethyl 2H-perfluoropropyl ether | 380-34-7 |
| Perfluoro(N-methylmorpholine) | 382-28-5 |
| 1H,1H,3H-Perfluorobutanol | 382-31-0 |
| Ammonium perfluorooctanoate | 3825-26-1 |
| Ethyl perfluoropentanyl ketone | 383177-55-7 |
| (Heptafluoropropyl)trimethylsilane | 3834-42-2 |
| 1-(Perfluorohexyl)-2-iodopropane | 38550-34-4 |
| 3-(Perfluorohexyl)-1,2-epoxypropane | 38565-52-5 |
| 3-(Perfluorooctyl)-1,2-propenoxide | 38565-53-6 |
| ((Perfluorodecyl)methyl)oxirane | 38565-54-7 |
| Potassium perfluorohexanesulfonate | 3871-99-6 |
| 8:2 Fluorotelomer sulfonic acid (8:2 FTS) | 39108-34-4 |
| Methyl perfluoro-3,6-dioxaheptanoate | 39187-41-2 |
| Methylperfluoro-2,5,8-trimethyl-3,6,9-trioxadodecanoic acid | 39187-47-8 |
| (Perfluoroheptyl)methyl methacrylate | 3934-23-4 |
| PFO2HxA | 39492-88-1 |
| PFO3OA | 39492-89-2 |
| PFO4DA | 39492-90-5 |
| PFO5DA | 39492-91-6 |
| 3H,3H-Perfluoro-2-butanone | 400-49-7 |
| Perfluoro-1-ethyl-3-propoxycyclohexane | 400626-82-6 |
| Perfluoro(1,3-dipropoxycyclohexane) | 400626-83-7 |
| 1,1,1,3,3-Pentafluorobutane | 406-58-6 |
| (Perfluorocyclohexyl)methyl prop-2-enoate | 40677-94-9 |
| (1H,1H-Perfluoroethyl)(2H-perfluoroethyl)ether | 406-78-0 |
| Bis(2,2,2-trifluoroethyl)amine | 407-01-2 |
| 2:2 Fluorotelomer iodide | 40723-80-6 |
| Perfluorodiacetamide | 407-24-9 |

TABLE A-continued

Exemplary PFAS Compounds and their CAS Numbers

| Compound Name and/or Description | CAS Registry No. |
|---|---|
| Trifluoroacetic anhydride | 407-25-0 |
| 2,2,2-Trifluoro-N-(2,2,2-trifluoroethyl)acetamide | 407-37-4 |
| 2,2,2-Trifluoroethyl trifluoroacetate | 407-38-5 |
| 7H-Perfluoroheptanoyl chloride | 41405-35-0 |
| Ethyl perfluoroheptanoate | 41430-70-0 |
| N-Ethylperfluorooctane sulfonamide (NEtFOSA) | 4151-50-2 |
| 1H,1H,9H-Perfluorononyl acrylate | 4180-26-1 |
| Perfluorohexanesulfonamide | 41997-13-1 |
| 1H,1H-Perfluoropropylamine | 422-03-7 |
| 2:1 Fluorotelomer alcohol | 422-05-9 |
| Pentafluoropropylamidine | 422-62-8 |
| 1H-Perfluoro-1,1-propanediol | 422-63-9 |
| Perfluoropropanoic acid (PFPrA) | 422-64-0 |
| 1-Bromoheptafluoropropane | 422-85-5 |
| Nonafluoro-1-iodobutane | 423-39-2 |
| PFPrS | 423-41-6 |
| 5:1 Fluorotelomer alcohol | 423-46-1 |
| 1H,1H-Perfluoroheptylamine | 423-49-4 |
| Perfluorooctanamide | 423-54-1 |
| 8:1 Fluorotelomer alcohol | 423-56-3 |
| Perfluoro-1-octanesulfonyl chloride | 423-60-9 |
| Perfluorodecyl iodide | 423-62-1 |
| 11:1 Fluorotelomer alcohol | 423-65-4 |
| 1H,1H,7H-Perfluoroheptyl 4-methylbenzenesulfonate | 424-16-8 |
| Methyl perfluorohexanoate | 424-18-0 |
| Ethyl perfluoropentanoate | 424-36-2 |
| Diethyl perfluoroglutarate | 424-40-8 |
| 1H,1H-Perfluorobutyl acrylate | 424-64-6 |
| Ethyl perfluoropropionate | 426-65-3 |
| 1H,1H-Perfluoropropyl methacrylate | 45115-53-5 |
| Perfluorooctanesulfonate | 45298-90-6 |
| ((Perfluoro-9-methyldecyl)methyl)oxirane | 47795-34-6 |
| (Perfluorohexyl)methyl methacrylate | 48076-44-4 |
| N-(3-(Dimethylamino)propyl) perfluorohexane sulfonamide | 50598-28-2 |
| Perfluorooctyl iodide | 507-63-1 |
| (Perfluoro-5-methylhexyl)ethyl 2-methylprop-2-enoate | 50836-66-3 |
| 2-Bromo-2-(Perfluorohexyl)ethene | 51249-64-0 |
| trans-1,2-Bis(perfluorohexyl)ethylene | 51249-67-3 |
| Perfluoromethyldecalin | 51294-16-7 |
| (1R,4R)-3-(Heptafluorobutyryl)-camphor | 51800-99-8 |
| Triethoxy((perfluorohexyl)ethyl)silane | 51851-37-7 |
| Perfluoroheptanoyl chloride | 52447-22-0 |
| Perfluorononanoyl chloride | 52447-23-1 |
| 2-(Perfluorobutyl)ethyl acrylate | 52591-27-2 |
| N-Methyl-N-trimethylsilylheptafluorobutyramide | 53296-64-3 |
| Bis(2,2,2-trifluoroethyl)sulfite | 53749-89-6 |
| 6:2 FTCA | 53826-12-3 |
| 10:2 FTCA | 53826-13-4 |
| 3-(Perfluoro-3-methylbutyl)-1,2-propenoxide | 54009-81-3 |
| Methyl 5H-perfluoropentanoate | 54822-22-9 |
| Fluorotelomer alcohol 2:2 | 54949-74-5 |
| Perfluoro-3,6,9-trioxaundecane-1,11-dioic acid | 55621-18-6 |
| Perfluoro-3,6-dioxaoctane-1,8-dioic acid | 55621-21-1 |
| 1-Bromoperfluorononane | 558-96-3 |
| Perfluorooct-1-ene | 559-14-8 |
| (Perfluorobutyryl)-2-thenoylmethane | 559-94-4 |
| N-(Phenylmethyl)perfluorobutanamide | 560-02-1 |
| 2H-Perfluoroisobutyric acid | 564-10-3 |
| Methyl 3H-perfluoroisopropyl ether | 568550-25-4 |
| Difluoromethyl 1H,1H-perfluoropropyl ether | 56860-81-2 |
| Difluoromethyl 2H-perfluoropropyl ether | 56860-85-6 |
| Bis(3,3,4,4,5,5,6,6,7,7,8,8,8-tridecafluorooctyl) hydrogen phosphate | 57677-95-9 |
| 6:2 Fluorotelomer phosphate monoester | 57678-01-0 |
| 2-(Perfluorooctyl)ethyl dihydrogen phosphate | 57678-03-2 |
| tris(Trifluoroethoxy)methane | 58244-27-2 |
| 2H-Hexafluoropropyl allyl ether | 59158-81-5 |
| Ammonium perfluoro-2-methyl-3-oxahexanoate | 62037-80-3 |
| 2,2,2-Trifluoroethyl triflate | 6226-25-1 |
| 1,1-bis(Trifluoromethyl)methoxy-2-ethanol | 63693-13-0 |
| Methyl perfluoro(3-(1-ethenyloxypropan-2-yloxy)propanoate) | 63863-43-4 |
| 1-Iodoperfluoropentane | 638-79-9 |
| 3H,3H-Perfluoropropyl triflate | 6401-00-9 |

TABLE A-continued

Exemplary PFAS Compounds and their CAS Numbers

| Compound Name and/or Description | CAS Registry No. |
|---|---|
| 1H,1H-Heptafluorobutyl triflate | 6401-01-0 |
| Fluorotelomer alcohol 6:2 | 647-42-7 |
| 2-(Perfluoro-3-methylbutyl)ethyl methacrylate | 65195-44-0 |
| Perfluoro-(2,5,8-trimethyl-3,6,9-trioxadodecanoic) acid | 65294-16-8 |
| Perfluorocyclohexanecarbonyl fluoride | 6588-63-2 |
| Tris(2,2,2-trifluoroethyl) borate | 659-18-7 |
| 5-Iodoperfluoro-3-oxapentanesulfonyl fluoride | 66137-74-4 |
| 1,2-Dibromohexafluoropropane | 661-95-0 |
| 2,2-bis(Trifluoromethyl)-2-hydroxyacetic acid | 662-22-6 |
| Heptafluorobutyramide | 662-50-0 |
| Ethyl pentafluoropropionyl acetate | 663-35-4 |
| Hexafluoroacetylacetone dihydrate | 66922-83-6 |
| (Perfluorododecyl)ethylene | 67103-05-3 |
| PFMOAA | 674-13-5 |
| 2-Chloro(perfluoro-2-methylpentane) | 67437-97-2 |
| Pentafluoroallyl fluorosulfate | 67641-28-5 |
| Heptafluoro-2-iodopropane | 677-69-0 |
| Methyl perfluorobutyl ketone | 678-18-2 |
| Fluorotelomer alcohol 8:2 | 678-39-7 |
| Bis(2-(perfluorooctyl)ethyl) hydrogen phosphate | 678-41-1 |
| Perfluorooctanedioic acid | 678-45-5 |
| 1,4-Divinylperfluorobutane | 678-65-9 |
| Hexafluoroglutaryl chloride | 678-77-3 |
| Perfluoroglutaryl difluoride | 678-78-4 |
| 1H,1H,5H,5H-Perfluoro-1,5-pentanediol diacrylate | 678-95-5 |
| 3-(Perfluoropropyl)propanol | 679-02-7 |
| Perfluoro-n-hexadecanoic acid (PFHxDA) | 67905-19-5 |
| 4H-Perfluorobutanoic acid | 679-12-9 |
| 1,1,2,2-Tetrafluoro-3-iodopropane | 679-87-8 |
| Methyl tetrafluoro-2-(trifluoromethyl)propionate | 680-05-7 |
| 3-(2,2,3,3-Tetrafluoropropoxy)prop-1-ene | 681-68-5 |
| Perfluorononanesulfonic acid (PFNS) | 68259-12-1 |
| N,O-Bis(trifluoroacetyl)hydroxylamine | 684-78-6 |
| Trifluoroacetyl triflate | 68602-57-3 |
| Trimethylsilyl perfluorobutanesulfonate | 68734-62-3 |
| EVE Acid | 69087-46-3 |
| Perfluorosuccinic anhydride | 699-30-9 |
| 8:2 FTUCA | 70887-84-2 |
| 6:2 FTUCA | 70887-88-6 |
| 10:2 FTUCA | 70887-94-4 |
| Perfluorotridecanoic acid (PFTriA) | 72629-94-8 |
| Perfluoro-3,6-dimethyl-1,4-dioxan-2-one | 7309-84-4 |
| 2-Allyloxyperfluoroethanesulfonyl fluoride | 73606-13-0 |
| Dichloromethyl((perfluorohexyl)ethyl)silane | 73609-36-6 |
| 2,2,3,3-Tetrafluoropropyl acrylate | 7383-71-3 |
| N-Methyl-bis-heptafluorobutyramide | 73980-71-9 |
| 2H-Perfluoroisopropyl 2-fluoroacrylate | 74359-06-1 |
| 2,2-Difluoroethyl triflate | 74427-22-8 |
| 2-(Perfluorooctyl)ethyldimethylchlorosilane | 74612-30-9 |
| Hydro-PS Acid | 749836-20-2 |
| Heptafluoropropyl iodide | 754-34-7 |
| Perfluorohexanal | 754-79-0 |
| Perfluorooctanesulfonamide (FOSA) | 754-91-6 |
| 1H,1H,10H,10H-Perfluorodecane-1,10-diol | 754-96-1 |
| Perfluorohex-1-ene | 755-25-9 |
| Fluorotelomer alcohol 3:2 | 755-40-8 |
| Perfluoro-2-methyl-3-pentanone | 756-13-8 |
| F-53B Major | 756426-58-1 |
| 4:2 Fluorotelomer sulfonic acid (4:2 FTS) | 757124-72-4 |
| Trifluoroacetic acid | 76-05-1 |
| 9H-Perfluorononanoic acid | 76-21-1 |
| F-53B Minor | 763051-92-9 |
| (Perfluoro-n-octyl)ethane | 77117-48-7 |
| Hydro-EVE Acid | 773804-62-9 |
| 3H-Perfluoro-2,2,4,4-tetrahydroxypentane | 77953-71-0 |
| 3H-Perfluoropentane-2,4-dione | 77968-17-3 |
| (Perfluorooctyl)ethyltrichlorosilane | 78560-44-8 |
| Trichloro((perfluorohexyl)ethyl)silane | 78560-45-9 |
| 2,3,3,3-Tetrafluoro-2-(perfluoropentoxy)propan-1-ol | 78693-85-3 |
| Perfluorododecanesulfonic acid (PFDoS) | 79780-39-5 |
| 2,2,2-Trifluoroethyl perfluorobutanesulfonate | 79963-95-4 |
| Perfluoro-4-isopropoxybutanoic acid (PFECA G) | 801212-59-9 |
| ((Perfluorooctyl)ethyl)phosphonic acid | 80220-63-9 |
| 3-(Perfluorobutyl)propanoic acid | 80705-13-1 |
| (Perfluoro-n-hexyl)ethane | 80793-17-5 |

TABLE A-continued

Exemplary PFAS Compounds and their CAS Numbers

| Compound Name and/or Description | CAS Registry No. |
|---|---|
| 3-(Perfluorohexyl)propanol | 80806-68-4 |
| 3-(Perfluoroheptyl)propanoic acid (7:3 FTCA) | 812-70-4 |
| 5H-Octafluoropentanoyl fluoride | 813-03-6 |
| Bis(perfluoroisopropyl)ketone | 813-44-5 |
| 2,2,3,3-Tetrafluoropropyl ether | 82914-35-0 |
| 1H,1H,2H,2H-Perfluorodecyltrimethoxysilane | 83048-65-1 |
| 3-(Perfluorobutyl)-1-propanol | 83310-97-8 |
| Cyclohexafluoropropane-1,3-bis(sulfonyl)imide | 84246-29-7 |
| (2H-Perfluoroethoxy)methyloxirane | 85567-21-1 |
| Perfluoro(2-bromoethyl vinyl ether) | 85737-06-0 |
| 2,4,6-Tris(pentafluoroethyl)-1,3,5-triazine | 858-46-8 |
| [2-(Perfluorohexyl)ethyl]trimethoxysilane | 85857-16-5 |
| Dimethoxymethyl((perfluorohexyl)ethyl)silane | 85857-17-6 |
| Perfluoro(4-methoxybutanoic acid) (PFMBA) | 863090-89-5 |
| Hexaflumuron | 86479-06-3 |
| 9-Chloro-perfluorononanoic acid | 865-79-2 |
| Fluorotelomer alcohol 10:2 | 865-86-1 |
| 1H,2H,2H-Perfluorobutane | 86884-16-4 |
| Bis(1H,1H-perfluoropropyl)amine | 883498-76-8 |
| 1H,1H-Perfluorobutyl perfluorobutanesulfonate | 883499-32-9 |
| 4-[3-(Perfluorobutyl)-1-propyloxy]benzyl alcohol | 892154-51-7 |
| (Perfluorooctyl)propanoyl chloride | 89373-67-1 |
| N-Methylperfluoroheptanamide | 89932-74-1 |
| 1H,1H,8H,8H-Perfluorooctane-1,8-diol | 90177-96-1 |
| 2(Perfluoro-2-propyl)ethanol | 90999-87-4 |
| 1H,1H,1H,2H-Perfluoro-2-heptanol | 914637-05-1 |
| Perfluoro-tert-butyl isobutyrate | 914637-43-7 |
| 2H,2H,3H,3H-Perfluorooctanoic acid (5:3 FTCA) | 914637-49-3 |
| 2,4,6-Tris(heptafluoropropyl)-1,3,5-triazine | 915-76-4 |
| Perfluoropinacol | 918-21-8 |
| 1,6-Dibromododecafluorohexane | 918-22-9 |
| 4,8-Dioxa-3H-perfluorononanoic acid (DONA) | 919005-14-4 |
| 2H-Perfluoro-2-propanol | 920-66-1 |
| MTP | 93449-21-9 |
| Methyl 4H-perfluorobutyl ketone | 93449-49-1 |
| 1-(Perfluorofluorooctyl)propane-2,3-diol | 94159-84-9 |
| Perfluoro-15-crown-5-ether | 97571-69-2 |
| 2-(2-Iodoethyl)perfluoropropane | 99324-96-6 |
| (2H-Perfluoropropyl)(1H,1H-perfluoroethyl)ether | 993-95-3 |
| 1,1,2-Trifluoro-1-methoxy-2-(trifluoromethoxy)ethane | 996-56-5 |
| Perfluoroheptanes (branched and linear) | |
| Methyl perfluoropentyl ketone | |
| 1H,1H,3H-Perfluoropropyl triflate | |
| Trifluoromethyl trifluoromethanesulfonate | |
| Nonafluoro-tert-butanol | |
| 4:4 Fluorotelomer alcohol | |
| 1H,1H,6H,6H-Perfluorohexane-1,6-diol diacrylate | |
| Perfluorobutanol | |

In some embodiments, the fluorinated compounds formed by oxidation of the one or more PFAS compounds in step a) can be detected by quadrupole mass spectrometer, nuclear magnetic resonance (NMR) analysis, fluorine-19 NMR (19F NMR) analysis, mass spectrometry (MS) analysis, tandem mass spectrometry (MS/MS) analysis, gas chromatography (GC) analysis, gas chromatography-mass spectrometry (GC-MS) analysis, gas chromatography-infrared spectroscopy (GC-IR) analysis, gas chromatography-flame ionization detection (GC-FID) analysis, liquid chromatography (LC) analysis, liquid chromatography-mass spectrometry (LC-MS) analysis, liquid chromatography-nuclear magnetic resonance (LC-NMR) analysis, high-performance liquid chromatography (HPLC) analysis, high-performance liquid chromatography-mass spectrometry (HPLC-MS) analysis, or a combination thereof.

EPA Method 537.1

In some embodiments, EPA method 537.1 is performed following the procedure below.

A water sample is fortified with surrogate analytes and passed through a solid phase extraction (SPE) cartridge containing polystyrenedivinylbenzene (SDVB) to extract the method analytes and surrogates. The compounds are eluted from the solid phase sorbent with a small amount of methanol. The extract is concentrated to dryness with nitrogen in a heated water bath, and then adjusted to a 1-mL volume with 96:4% (vol/vol) methanol:water and addition of the internal standards. A 10-μL injection is made into a liquid chromatogram (LC) equipped with a C18 column that is interfaced to a mass-spectrometry/mass-spectrometry (MS/MS). The analytes are separated and identified by comparing the acquired mass spectra and retention times to reference spectra and retention times for calibration standards acquired under identical LC/MS/MS conditions. The concentration of each analyte is determined by using the internal standard technique.

Surrogate analytes are added to all field and quality control (QC) samples to monitor the extraction efficiency of the method analytes. The surrogate analyte may be perfluoro-n-[1,2-13C2]hexanoic acid (13C2-PFHxA), perfluoro-n-[1,2-13C2]decanoic acid (13C2-PFDA), N-deuterioethylperfluoro-1-octanesulfonamidoacetic acid (d5-NEtFOSAA), or tetrafluoro-2-heptafluoropropoxy13C3-propanoic acid (13C3-HFPO-DA).

EPA Method 1633

In some embodiments, EPA method 1633 is performed following the procedure below.

Environmental samples are prepared and extracted using method-specific procedures. Sample extracts are subjected to cleanup procedures designed to remove interferences. Analytes of the sample extracts are conducted by LC-MS/MS in the multiple reaction monitoring (MRM) mode. Sample concentrations are determined by isotope dilution or extracted internal standard quantification using isotopically labeled compounds added to the samples before extraction.

Aqueous samples are spiked with isotopically labeled standards, extracted using solid-phase extraction (SPE) cartridges and undergo cleanup using carbon before analysis.

Solid samples are spiked with isotopically labeled standards, extracted into basic methanol, and cleaned up by carbon and SPE cartridges before analysis.

Tissue samples are spiked with isotopically labeled standards, extracted in potassium hydroxide and acetonitrile followed by basic methanol, and cleaned up by carbon and SPE cartridges before analysis.

This method measures the analytes as either their anions or neutral forms. The default approach uses of the method is to detect the analytes in their acid or neutral forms, although the differences between the anion and acid form concentrations are minimal.

Individual PFAS analytes are identified through peak analysis of the quantification and confirmation ions, where applicable.

Quantitative determination of target analyte concentrations is made with respect to an isotopically labeled PFAS standard; the concentrations are then used to convert raw peak areas in sample chromatograms to final concentrations.

Results for target analytes are recovery corrected by the method of quantification (i.e., either isotope dilution or extracted internal standard quantification). Isotopically labeled compound recoveries are determined by comparison to the responses of one of seven non-extracted internal standards (a.k.a., the "recovery" standards) and are used as general indicators of overall analytical quality.

EXAMPLES

Example 1. Extraction of Yarn and Fiber for Analysis

For all Examples 1-3, all boiling flasks and beakers were soaked in Alconox solution overnight and rinsed: once with distilled water, once with fuming nitric acid, once with distilled water, three times with methylene chloride, and three times with methanol. After rinsing, the boiling flasks and beakers were dried either by nitrogen stream or inversion. All distillation columns were rinsed three times with methanol and then dried either by nitrogen stream or inversion.

Yarn or fiber sample (50 g) are weighed and added to a chromatography column. The column was rinsed with methanol (3×60 mL). The elutriate was collected in a boiling flask and concentrated to 50 mL using low temperature (under about 100° C.) heating to evaporate the methanol.

The concentrated sample can be oxidized based on the procedures described in Examples 2 and 3.

Example 2. Oxidation of Sample with Persulfate

Sample (50 g) was weighed into a boiling flask. Sodium hydroxide (200 mL, 1 M) and sodium persulfate (10 g) were added sequentially. The sample was heated in an oil bath at 75° C. for 24 h (the hot plate was heated to approx. 155° C.). The sample was removed and cooled to room temperature. The solution was decanted into a beaker, leaving any solid materials in the boiling flask. Glacial acetic acid (8 mL) was added to the solution. The solution was diluted with distilled water to a total volume of 500 mL. The pH was adjusted to 4.0 by addition of either sodium hydroxide (1 M) or glacial acetic acid. About 250 mL of the resulting solution were added by pipette to an HDPE, leaving behind any solid materials, for analysis by EPA methods 537.1 or 1633.

Example 3. Oxidation of Sample with a Fenton's Reagent

Caution was taken to maintain a temperature of 20° C. or less for this oxidation, as the addition of peroxide, as described below, is an exothermic process.

To prepare a Fenton's reagent, iron (II) sulfate (10 g) was weighed into a boiling flask. Distilled water (50 mL) was added and the flask was swirled to dissolve all of the iron (II) sulfate. The resulting solution was cooled in an ice bath to a temperature of about 5° C. Aqueous hydrogen peroxide (50 mL, 50%) was slowly added by pipette into the iron (II) sulfate solution, while maintaining a temperature of under 150° C. The resulting solution was allowed to cool to 50° C.

Sample (10 g/mL) was added slowly to the solution of a Fenton's reagent, while continuing to cool the boiling flask in an ice bath. After addition of the sample, the resulting solution was allowed to warm slowly. The solution was heated to room temperature. A solution of methanol in water (50%) was added to the solution to give a final volume of 500 mL. About 250 mL of the resulting solution were added by pipette to an HDPE, leaving behind any solid materials, for analysis by EPA methods 537.1 or 1633.

Example 4. Summary of Analysis of Samples

Samples were prepared and evaluated using the methods described in Examples 1-3 to determine the overall PFAS content. Additional samples were evaluated using the proprietary total oxidizable precursor (TOP) and total organic fluorine (TOF) assays provided by Eurofins USA. The comparative results are presented below in Table B. The "Sample Description" column describes source and content of the sample, the "Method" column describes which exemplary procedure was used to prepare and analyze the sample, the "Total Analyte" column reports the total detected PFAS analyte in each sample in parts per trillion (ppt), and the remaining columns report the specific PFAS analyte detected in each sample in ppt.

TABLE B

Summary of Analysis of Samples

| Sample No. | Sample Description | Method | Total Analyte (ppt) | Individual Analyte Concentration (ppt) |
|---|---|---|---|---|
| 1 | Lauryl Alcohol | 537.1 | 0 | N/A |
| | | 2 | 32.1 | PFPeA (19), PFHxA (6.1), PFHpA (1.2), PFOA (1.5), PFBA (4.3) |
| 2 | Calfax DB-45 Surfactant | TOF | 0 | N/A |
| | | TOP | 0 | N/A |
| | | 2 | 370 | NEtFOSAA (370) |
| | | 4 | 17000 | PFBA (17000) |
| 3 | Disperse Blue Dye (Coralene Blue ERAM) | 537.1 | 0 | N/A |
| | | 2 | 0 | N/A |
| 4 | Disperse Red Dye (Coralene Red B-FD) | 537.1 | 0 | N/A |
| | | 2 | 0 | N/A |
| 5 | Disperse Yellow Dye (Coralene Yellow Y3G Mix) | 537.1 | 0 | N/A |
| | | 2 | 907 | NMeFOSE (160), 7:3 FTCA (170), PFBA (380), 11CI-PF3OUcS (27), NEtFOSE (170) |
| 6 | Boiler Chemicals (D7 Nalco, Nexguard) | 537.1 | 292 | PFOA (5.6), PFOS (9.2), PFBS (4.2), FOSA (23), NEtFOSAA (250) |
| | | TOP | 15.7 | PFPeA (2.8), PFOS (8.4), PFBS (4.5) |
| | | 2 | 354.77 | 6:2 FTS (350), PFHxA (1.5), PFHpA (0.9), PFOA (1.3), 4:2 FTS (1.1) |
| 7 | Topical Anti-Soil Treatment (ICT 1260L) | 537.1 | 0 | N/A |
| | | TOP | 5600 | PFPeA (1900), PFHxA (1100), PFBA (2600) |
| | | 2 | 4536.1 | 5:3 FTCA (1.7), 6:2 FTS (460), PFPeA (2.7), PFHxA (8.9), PFHpA (17), PFOA (4.9), PFNA (8.8), PFDA (5.3), PFHxS (3.1), PFOS (3900), PFBS (2.1), PFPeS (1.5), PFMBA (1.8), ADONA (2.6), PFNS (3.4), PFDS (1.9), 4:2 FTS (2.3), 9CI-PF3ONS (3.2), 11CI-PF3OUcS (1.9), PFMPA (2.2), PFEESA (1.8), 8:2 FTS (99) |
| 8 | Stainblocker (Myalon 3S) | 2 | 2100 | 6:2 FTS (2100) |
| 9 | Topical Anti-Soil Treatment (Permaseal 50C) | 537.1 | 0 | N/A |
| | | TOP | 5400 | PFPeA (4200), PFTeA (1200) |
| | | TOP | 2700 | PFPeA (1200), PFBA (1500) |
| | | TOP | 0 | N/A |
| | | TOP | 0 | N/A |
| | | TOP | 0 | N/A |
| | | 2 | 1100 | 6:2 FTS (1100) |
| 10 | Sulfamic Acid | 537.1 | 3.4 | PFOS (3.2), PFBS (0.2) |
| | | 2 | 14.7 | PFPeA (9), PFHxA (3.1), |

TABLE B-continued

Summary of Analysis of Samples

| Sample No. | Sample Description | Method | Total Analyte (ppt) | Individual Analyte Concentration (ppt) |
|---|---|---|---|---|
| | | | | PFHpA (0.3), PFBA (2.3) |

As shown in Table D, higher concentrations of analytes were detected when using the oxidative methods described in Example 2 before analysis using EPA methods 537.1 and 1633, compared to analyzing the samples using EPA methods 537.1 and 1633 without first oxidizing the samples. In most cases shown in Table D, EPA method 537.1 was not able to detect any of the PFAS analytes in the samples, whereas pre-oxidation using the methods described in Example 2 led to higher detected concentrations of PFAS compounds.

Compared to the proprietary TOF assay, the methods described in Example 2 resulted in a higher detected concentrations of PFAS compounds (see Sample No. 2).

Compared to the proprietary TOP assay, the methods described in Example 2 resulted in the detection of higher concentrations of PFAS compounds in Sample Nos. 2 and 6, comparable detection in Sample No. 7, and lower detection in Sample No. 9. The TOP assay was performed on Sample No. 9 five times, and PFAS compounds were only detected in two instances.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of detecting a presence of one or more perfluoroalkyl or polyfluoroalkyl substance (PFAS) compounds in a sample, comprising:

a) treating the sample with an oxidizing agent to form a mixture, wherein the oxidizing agent in step a) is a persulfate;

b) maintaining the mixture for a reaction time at a reaction temperature, wherein the reaction time is from about 6 h to about 48 h and the reaction temperature is from about 50° C. to about 100° C.;

c) collecting fluorinated compounds formed by oxidation of the one or more PFAS compounds in steps a) and b) in an aqueous mixture;

and d) detecting the fluorinated compounds by a process comprising subjecting the mixture obtained in step c) to EPA method 537.1 or EPA method 1633;

wherein at least some of the fluorinated compounds detected in step d) are different from fluorinated compounds detected by a second method that does not comprise steps a) to c).

2. The method of claim 1, wherein the sample further comprises one or more surfactants.

3. The method of claim 1, wherein the persulfate is sodium persulfate, potassium persulfate, ammonium persulfate, sodium peroxomonosulfate, or potassium peroxymonosulfate.

4. The method of claim 1, wherein the persulfate is sodium persulfate.

5. The method of claim 1, the method further comprising treating the sample with a base to form a pre-mixture before step a), and treating the pre-mixture with an oxidizing agent to form a mixture in step a).

6. The method of claim 5, wherein the base is a hydroxide, wherein the base is potassium hydroxide (KOH), sodium hydroxide (NaOH), barium hydroxide ($Ba(OH)_2$), cesium hydroxide ($Cs(OH)_2$), strontium hydroxide ($Sr(OH)_2$), calcium hydroxide ($Ca(OH)_2$), lithium hydroxide (LiOH), or rubidium hydroxide (RbOH).

7. The method of claim 5, wherein the base is present in a concentration of about 0.1 M to about 10 M.

8. The method of claim 5, wherein the base is aqueous sodium hydroxide (NaOH) at a concentration of about 1 M.

9. The method of claim 5, wherein:
the base is aqueous sodium hydroxide (NaOH) at a concentration of about 0.1 M to about 10 M; and
the oxidizing agent in step a) is sodium persulfate.

10. The method of claim 5, wherein:
the base is aqueous sodium hydroxide (NaOH) at a concentration of about 1 M;
the oxidizing agent in step a) is a sodium persulfate;
the reaction temperature in step b) is about 75° C.; and
the reaction time in step b) is about 24 h.

11. The method of claim 1, wherein the reaction temperature in step b) is about 75° C.

12. The method of claim 1, wherein the reaction time in step b) is about 24 h.

13. The method of claim 1, wherein the aqueous mixture in step c) is an aqueous solution.

14. The method of claim 1, wherein the second method comprises subjecting a sample to EPA method 537.1 or EPA method 1633.

15. A method of detecting a presence of one or more perfluoroalkyl or polyfluoroalkyl substance (PFAS) compounds in a yarn or fiber sample, comprising:
a) treating the sample with an oxidizing agent to form a mixture, wherein the oxidizing agent in step a) is a persulfate;
b) maintaining the mixture for a reaction time at a reaction temperature, wherein the reaction time is from about 6 h to about 48 h and the reaction temperature is from about 50° C. to about 100° C.;
c) collecting fluorinated compounds formed by oxidation of the one or more PFAS compounds in steps a) and b) in an aqueous mixture;
and
d) detecting the fluorinated compounds by a process comprising subjecting the mixture obtained in step c) to EPA method 537.1 or EPA method 1633;
wherein at least some of the fluorinated compounds detected in step d) are different from fluorinated compounds detected by a second method that does not comprise steps a) to c).

16. The method of claim 15, wherein:
the sample further comprises one or more surfactants;
the sample is treated with a base to form a pre-mixture before step a), and the pre-mixture is treated with an oxidizing agent to form a mixture in step a);
the base is aqueous sodium hydroxide (NaOH) at a concentration of about 0.1 M to about 10 M; and
the oxidizing agent in step a) is sodium persulfate.

17. The method of claim 15, wherein:
the sample further comprises one or more surfactants;
the sample is treated with a base to form a pre-mixture before step a), and the pre-mixture is treated with an oxidizing agent to form a mixture in step a);
the base is aqueous sodium hydroxide (NaOH) at a concentration of about 1 M;
the oxidizing agent in step a) is a sodium persulfate;
the reaction temperature in step b) is about 75° C.; and
the reaction time in step b) is about 24 h.

18. A method of detecting a presence of one or more perfluoroalkyl or polyfluoroalkyl substance (PFAS) compounds in a sample, comprising:
a) treating the sample with an oxidizing agent to form a mixture, wherein the oxidizing agent in step a) is a Fenton's reagent;
b) maintaining the mixture for a reaction time at a reaction temperature;
wherein step b) further comprises cooling the mixture to a first reaction temperature and then heating the mixture to a second reaction temperature;
c) collecting fluorinated compounds formed by oxidation of the one or more PFAS compounds in steps a) and b) in an aqueous mixture;
and
d) detecting the fluorinated compounds by a process comprising subjecting the mixture obtained in step c) to EPA method 537.1 or EPA method 1633;
wherein at least some of the fluorinated compounds detected in step d) are different from fluorinated compounds detected by a second method that does not comprise steps a) to c).

19. The method of claim 18, wherein the first reaction temperature in step b) is from about 0° C. to about 15° C.

20. The method of claim 18, wherein the second reaction temperature in step b) is from about 15° C. to about 25° C.

21. The method of claim 18, wherein the second reaction temperature in step b) is about 20° C.

22. The method of claim 18, wherein the reaction time in step b) is from about 10 min to about 4 h.

23. The method of claim 18, wherein:
step b) further comprises cooling the mixture to a first reaction temperature of from about 0° C. to about 15° C. and then heating the mixture to a second reaction temperature of from about 15° C. to about 25° C.; and
the reaction time in step b) is from about 10 min to 4 h.

24. The method of claim 18, wherein:
step b) further comprises cooling the mixture to a first reaction temperature of about 5° C. and then heating the mixture to a second reaction temperature of about 20° C.; and
the reaction time in step b) is about 2 h.

25. The method of claim 18, wherein the second method comprises subjecting a sample to EPA method 537.1 or EPA method 1633.

26. A method of detecting a presence of one or more perfluoroalkyl or polyfluoroalkyl substance (PFAS) compounds in a yarn or fiber sample, comprising:
a) treating the sample with an oxidizing agent to form a mixture, wherein the oxidizing agent in step a) is a Fenton's reagent;
b) maintaining the mixture for a reaction time at a reaction temperature;
wherein step b) further comprises cooling the mixture to a first reaction temperature and then heating the mixture to a second reaction temperature;
c) collecting fluorinated compounds formed by oxidation of the one or more PFAS compounds in steps a) and b) in an aqueous mixture;

and d) detecting the fluorinated compounds by a process comprising subjecting the mixture obtained in step c) to EPA method 537.1 or EPA method 1633;

wherein at least some of the fluorinated compounds detected in step d) are different from fluorinated compounds detected by a second method that does not comprise steps a) to c).

27. The method of claim 26, wherein:

the sample further comprises one or more surfactants;

step b) further comprises cooling the mixture to a first reaction temperature of from about 0° C. to about 15° C. and then heating the mixture to a second reaction temperature of from about 15° C. to about 25° C.; and the reaction time in step b) is from about 10 min to 4 h.

28. The method of claim 26, wherein:

the sample further comprises one or more surfactants;

step b) further comprises cooling the mixture to a first reaction temperature of about 5° C. and then heating the mixture to a second reaction temperature of about 20° C.; and the reaction time in step b) is about 2 h.

* * * * *